(12) United States Patent
Smith et al.

(10) Patent No.: US 10,071,511 B2
(45) Date of Patent: Sep. 11, 2018

(54) METHOD AND DEVICE FOR PRODUCING TEMPORARY KNEE JOINT SPACERS WITH STEMS OF VARIOUS SIZES

(71) Applicant: BIOMET MANUFACTURING LLC, Warsaw, IN (US)

(72) Inventors: Daniel B. Smith, Warsaw, IN (US); Tayler E. Kreider, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 550 days.

(21) Appl. No.: 14/104,308

(22) Filed: Dec. 12, 2013

(65) Prior Publication Data

US 2014/0159282 A1    Jun. 12, 2014

Related U.S. Application Data

(60) Provisional application No. 61/736,386, filed on Dec. 12, 2012.

(51) Int. Cl.
  *A61F 2/38*    (2006.01)
  *B29C 45/00*   (2006.01)
  (Continued)

(52) U.S. Cl.
  CPC ...... *B29C 45/0001* (2013.01); *A61F 2/30942* (2013.01); *A61F 2/38* (2013.01);
  (Continued)

(58) Field of Classification Search
  None
  See application file for complete search history.

(56) References Cited

U.S. PATENT DOCUMENTS

| 6,155,812 A   | 12/2000 | Smith et al. |
| 6,361,731 B1* | 3/2002  | Smith ................. A61F 2/30942 264/271.1 |

(Continued)

FOREIGN PATENT DOCUMENTS

| CN | 102548510 A | 7/2012 |
| CN | 104902851 A | 9/2015 |

(Continued)

OTHER PUBLICATIONS

International Search Report and Written Opinion dated Dec. 12, 2013 for related application No. PCT/US2013/074757.

(Continued)

*Primary Examiner* — Jacob T Minskey
(74) *Attorney, Agent, or Firm* — Schwegman Lundberg & Woessner, P.A.

(57) ABSTRACT

A cement mold assembly configured to form a temporary implant for use in delivering antibiotics to an infected site can includes a first mold and a second mold. The first mold can have an open end and an inner wall. The first mold can define a tibial component forming cavity including a platform forming cavity and a stem forming cavity. The second mold can have a body portion configured to be slidably and progressively receivable by the inner wall into the tibial component forming cavity in a direction toward the closed end. Progressive advancement of the second mold into the tibial component forming cavity urges cement within the tibial component forming cavity against the body portion and the inner wall to form a unitary tibial component having a tibial tray portion formed by the platform forming cavity and a stem portion formed by the stem forming cavity.

19 Claims, 7 Drawing Sheets

(51) Int. Cl.
*B29C 45/26* (2006.01)
*A61F 2/30* (2006.01)
*A61F 2/46* (2006.01)

(52) U.S. Cl.
CPC ............ *A61F 2/4684* (2013.01); *B29C 45/26* (2013.01); *A61F 2/389* (2013.01); *A61F 2/3859* (2013.01); *A61F 2002/30329* (2013.01); *A61F 2002/30604* (2013.01); *A61F 2002/30672* (2013.01); *A61F 2002/30677* (2013.01); *A61F 2002/30957* (2013.01); *A61F 2220/0025* (2013.01); *A61F 2310/00353* (2013.01)

(56) References Cited

U.S. PATENT DOCUMENTS

| | | |
|---|---|---|
| 6,942,475 B2 | 9/2005 | Ensign et al. |
| 7,427,296 B2 | 9/2008 | Evans |
| 7,429,346 B2 | 9/2008 | Ensign et al. |
| 7,637,729 B2 | 12/2009 | Hartman et al. |
| 7,789,646 B2 | 9/2010 | Haney et al. |
| 7,867,426 B2 | 1/2011 | Ziran et al. |
| 9,433,506 B2 | 9/2016 | Lomicka et al. |
| 2004/0036189 A1 | 2/2004 | Ensign et al. |
| 2009/0295035 A1 | 12/2009 | Evans |
| 2010/0102484 A1 | 4/2010 | Haney et al. |
| 2012/0193509 A1 | 8/2012 | Evans |

FOREIGN PATENT DOCUMENTS

| | | | |
|---|---|---|---|
| CN | 107361882 A | | 11/2017 |
| DE | 102011104808 | | 12/2012 |
| EP | 2532323 A1 | | 12/2012 |
| JP | 06238680 A | | 8/1994 |
| JP | 2012507343 A | | 3/2012 |
| WO | WO-0003855 A1 | | 1/2000 |
| WO | WO-2004082521 A2 | | 9/2004 |
| WO | WO-2012/158618 | | 11/2012 |
| WO | WO-2014093672 A1 | | 6/2014 |

OTHER PUBLICATIONS

"European Application Serial No. 13818876.8, Office Action dated Aug. 20, 2015", 2 pgs.
"European Application Serial No. 13818876.8, Response filed Feb. 29, 2016 to Office Action dated Aug. 20, 2015", 13 pgs.
"International Application Serial No. PCT/US2013/074757, International Preliminary Report on Patentability dated Jun. 25, 2015", 10 pgs.
"Chinese Application Serial No. 201380065344.4, Office Action dated May 17, 2016", With English Translation, 19 pgs.
"Chinese Application Serial No. 201380065344.4, Response filed Sep. 30, 2016 to Office Action dated May 17, 2016", W/ English Translation of Claims, 17 pgs.
"Chinese Application Serial No. 201380065344.4, Office Action dated Jan. 13, 2017", With English Translation, 11 pgs.
"European Application Serial No. 16183586.3, Extended European Search Report dated Feb. 16, 2017", 7 pgs.
"Chinese Application Serial No. 201380065344.4, Response Filed Mar. 27, 2017 to Office Action dated Jan. 13, 2017", With English Translation of Claims, 39 pgs.
"European Application Serial No. 16183586.3, Response filed Sep. 21, 2017 to Extended European Search Report dated Feb. 16, 2017", 21pgs.
"Japanese Application Serial No. 2015-547560, Office Action dated May 23, 2017", With English Translation, 5 pgs.
"Japanese Application Serial No. 2015-547560, Office Action dated Sep. 26, 2017", With English Translation, 2 pgs.
"Japanese Application Serial No. 2015-547560, Response filed Aug. 15, 2017 to Office Action dated May 23, 2017", With English Translation, 25 pgs.

* cited by examiner

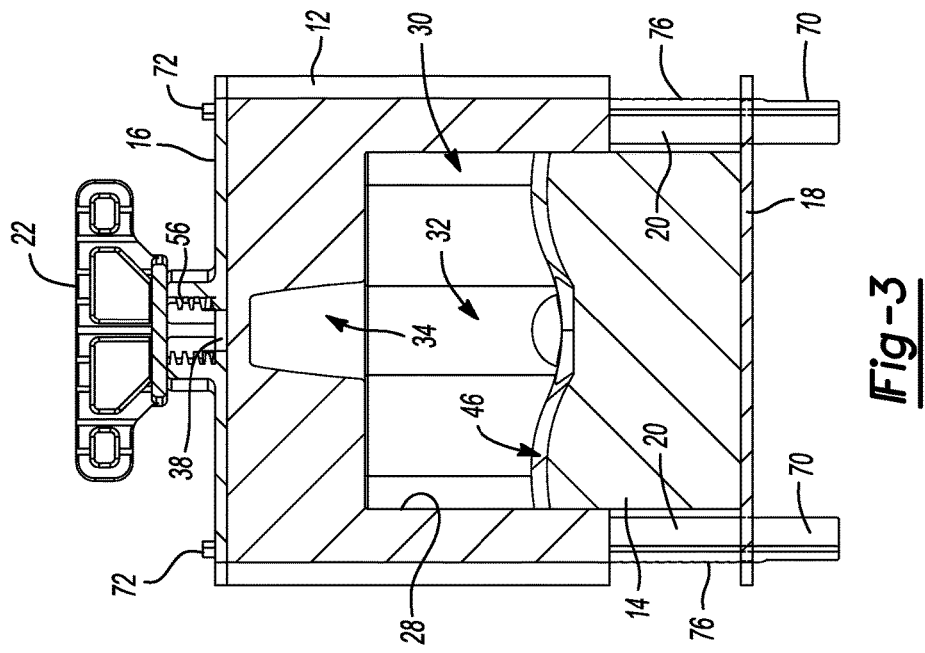
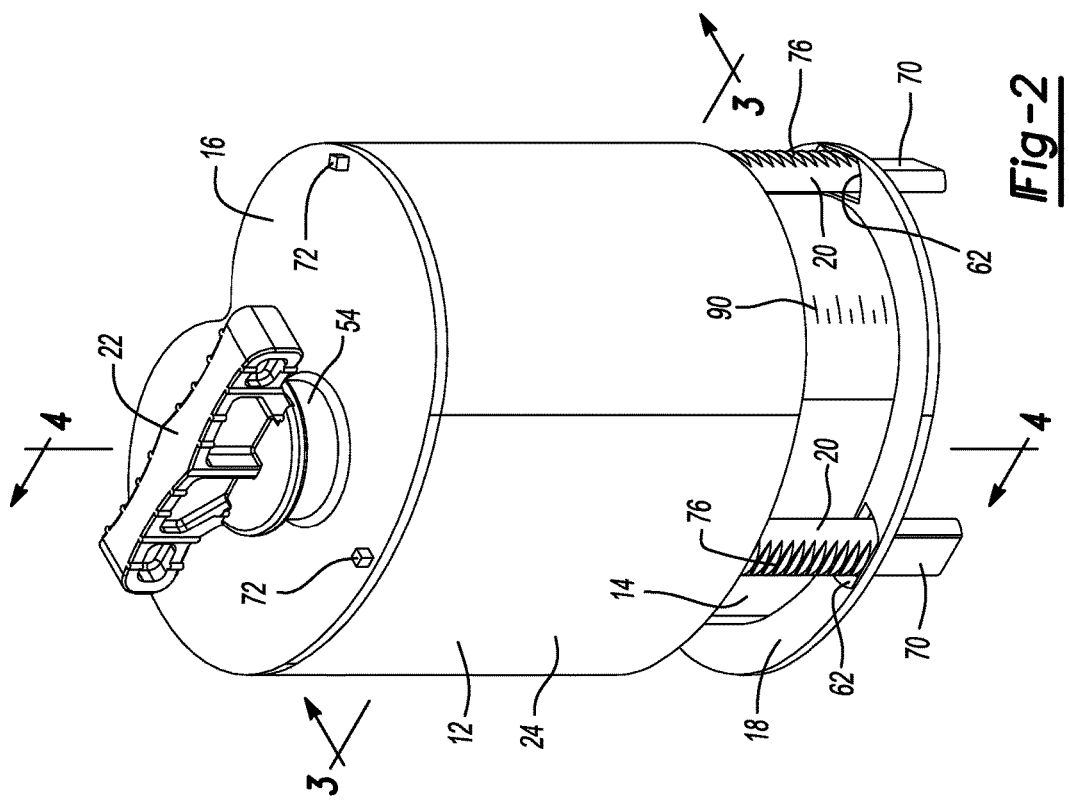

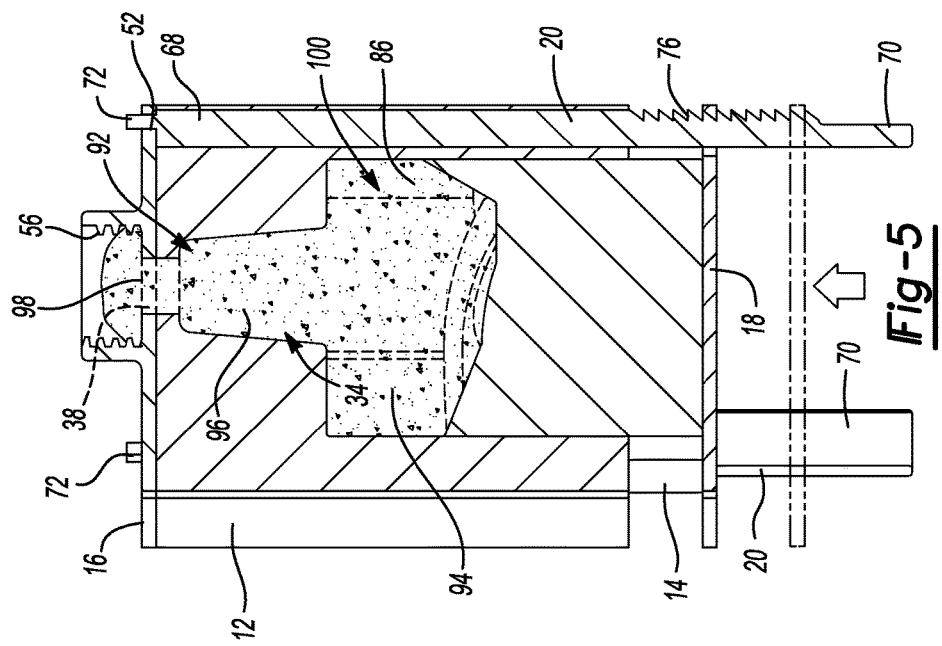
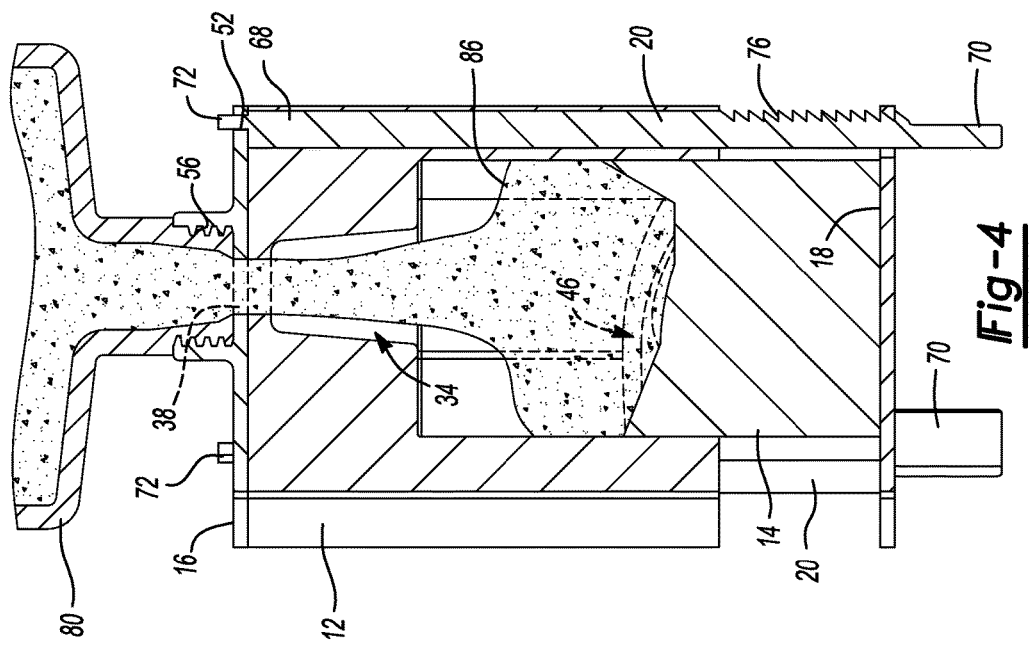

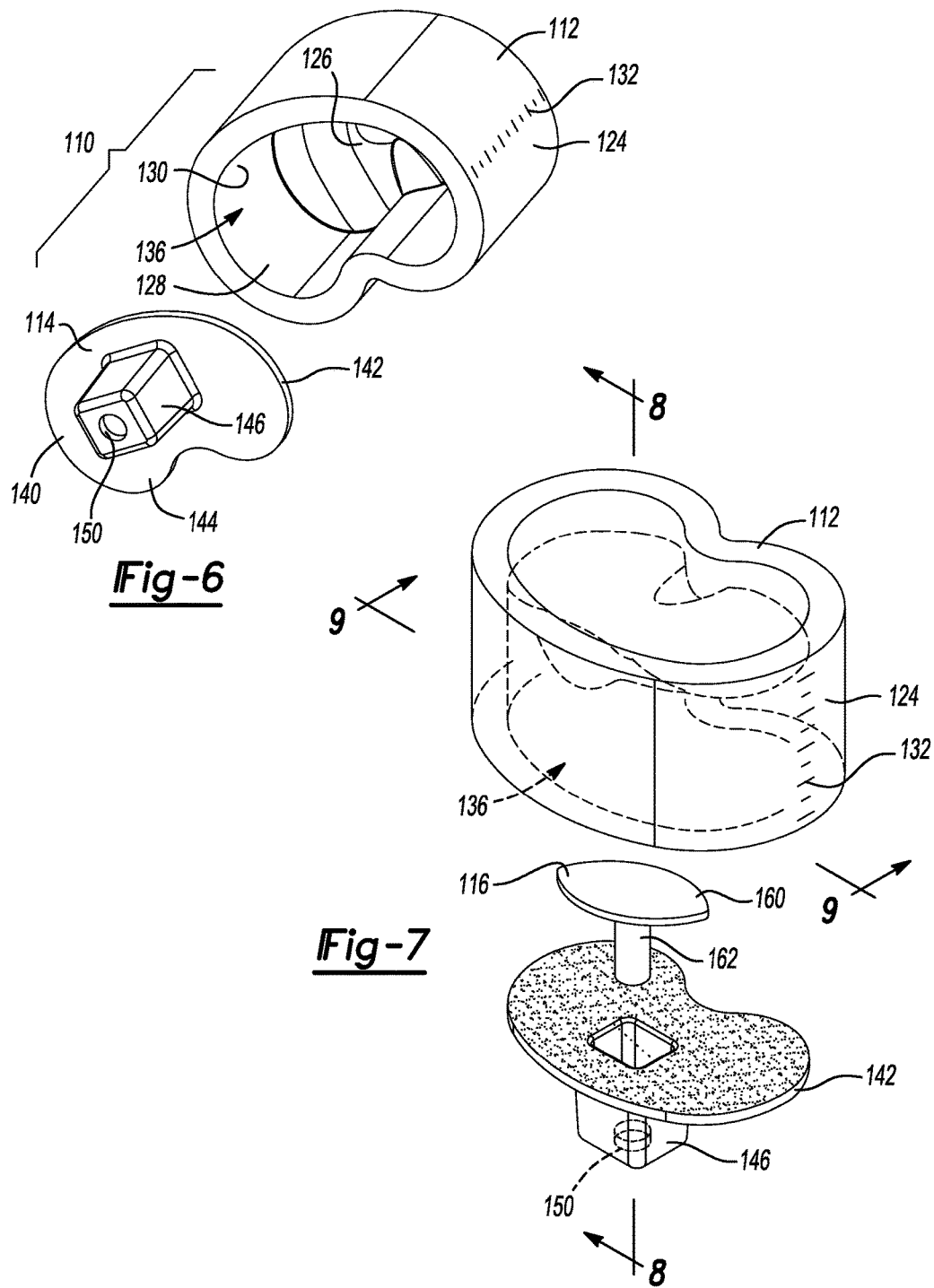

METHOD AND DEVICE FOR PRODUCING TEMPORARY KNEE JOINT SPACERS WITH STEMS OF VARIOUS SIZES

CROSS-REFERENCE TO RELATED APPLICATIONS

This application claims the benefit of U.S. Provisional Application No. 61/736,386, filed on Dec. 12, 2012. The entire disclosure of the above application is incorporated herein by reference.

FIELD

This disclosure relates generally to orthopedic implants for use in orthopedic surgical procedures and, more particularly, to cement molds for use in forming temporary orthopedic implants used in orthopedic surgical procedures.

BACKGROUND

This section provides background information related to the present disclosure which is not necessarily prior art.

A natural joint may undergo degenerative changes due to a variety of etiologies. When these degenerative changes become so far advanced and irreversible, it may ultimately become necessary to replace the natural joint with a joint prosthesis. However, due to any number of reasons, a small portion of patients that undergo such orthopedic surgical procedures suffer from infections at the surgical site and generally around the implanted joint prosthesis. In order to eradicate or clear such an infection in a two-stage reimplantation, the implanted joint prosthesis is generally removed, the site is thoroughly debrided and washed, antibiotics are applied to the infected site until the infection is eliminated, and a new revision type joint prosthesis is then implanted during a subsequent orthopedic surgical procedure. Systemic antibiotics may also act as an adjunct to local antibiotic delivery. Another technique, more popular in Europe, is the one stage reimplantation in which the prosthesis is removed, the site is debrided and washed and a new permanent implant is cemented in place using antibiotic loaded bone cement.

The currently available techniques for delivering the antibiotic to the infected joint area include mixing appropriate bone cement, such as (PMMA) poly-methyl-methacrylate, with an antibiotic, such as gentamicin, and applying the mixture to the infected joint area. Another technique involves the use of pre-loaded antibiotic cement beads which are retained on a string or wire. The antibiotic loaded bone cement is packed into the voids created by the explanted joint prosthesis while the joint is distracted or the string of antibiotic loaded beads are dropped into the respective voids. During this period, the antibiotic leaches out from the bone cement and into the infected area, while the patient may be left substantially non-ambulatory or bed-ridden with very limited mobility. In addition, soft tissue contraction in the area about the joint may cause a more difficult revision surgery since the remaining bone portion is smaller than the explanted joint prosthesis. Moreover, the above techniques may also suffer from the disadvantage of sometimes being difficult or messy to use during the orthopedic surgical procedure. This disadvantage is primarily exhibited during the use of the antibiotic loaded bone cement in a doughy state and attempting to fill the appropriate region in the distracted joint area.

SUMMARY

This section provides a general summary of the disclosure, and is not a comprehensive disclosure of its full scope or all of its features.

A cement mold assembly configured to form a temporary implant for use in delivering antibiotics to an infected site can include a first mold and a second mold. The first mold can have an open end and an inner wall. The first mold can define a tibial component forming cavity including a platform forming cavity and a stem forming cavity. The second mold can have a body portion configured to be slidably and progressively receivable by the inner wall into the tibial component forming cavity in a direction toward the closed end. Progressive advancement of the second mold into the tibial component forming cavity urges cement within the tibial component forming cavity against the body portion and the inner wall to form a unitary tibial component having a tibial tray portion formed by the platform forming cavity and a stem portion formed by the stem forming cavity.

According to additional features, the first mold can define a port opposite the open end that is configured to receive cement therethrough. The cement mold assembly can further comprise a first plate and a second plate positioned outboard of the first and second molds, respectively. The cement mold assembly can further comprise at least two rods connected between the first and second plates. The rods and the first and second plates can be selectively and progressively indexable. The first and second plates can be movable in discrete increments toward each other while the second mold is progressively advanced into the tibial component forming cavity. The rods can include teeth formed thereon that cooperatively engage an opposing surface on one of the first and second plates. The body of the second mold can include a geometry that substantially corresponds to a tibial bearing surface. The first mold can be formed of silicone. The second mold can be formed of silicone.

A cement mold assembly configured to form a temporary implant for use in delivering antibiotics to an infected site can include a first mold and a second mold. The first mold can have a first closed end, a second open end, and a sidewall. The first mold can define a cavity. The second mold can have a base portion and a cannulated member extending therefrom. The base portion can have a footprint complementary to the sidewall of the first mold such that the second mold is slidably and progressively receivable by the sidewall into the cavity in a direction toward the closed end. Progressive advancement of the second mold into the cavity can urge the cement within the cavity into the cannulated member. The first mold can cooperate with the second mold to form a unitary tibial component having a tibial tray portion formed by the cavity and a stem portion formed by the cannulated member.

According to additional features, the cement mold assembly can further comprise a reinforcement member configured to be placed at least partially within the cavity prior to progressive advancement of the second mold into the cavity. The reinforcement member can be configured to be molded into the unitary tibial component. The reinforcement member can comprise a first lateral portion that generally opposes a first closed end and a second longitudinal portion that is received by the cannulated member. The cannulated member can have a generally rectangular cross-section. The base portion of the second mold can have a textured surface. The first mold can include gradations on the sidewall. The first mold can be formed of silicone. The second mold can be formed of polyethylene. The reinforcement member can be formed of biocompatible metal.

According to still other features, a cement mold assembly configured to form a temporary implant for use in delivering antibiotics to an infected site can comprise a mold body having an outer sidewall and an inner sidewall that cooperate to define a cavity. The inner sidewall can be operable to define a shape of the temporary implant. The mold body can include articulating forming portions and a stem forming portion. The articulating and stem forming portions can cooperate to form a unitary femoral component having an articulating portion formed by the articulating forming portion and a stem portion formed by the stem forming portion.

According to other features, the stem forming portion can be removably coupled to the articulating forming portion. The stem forming portion can be threadably coupled to the articulating forming portion. The stem forming portion can have a first end defining first threads and a second end defining second threads. The first threads can be configured to threadably couple with the articulating forming portion. The second threads can be configured to threadably couple with a cement delivery device. The mold body can define vents therethrough. According to additional features, a reinforcement member can be configured to be placed at least partially within the cavity. The reinforcement member can be configured to be molded into the unitary femoral component.

A method of making a temporary implant for use in delivering antibiotics to an infected site can include, providing a first mold that defines an implant forming cavity collectively defined by an implant body forming cavity and an implant stem forming cavity. A second mold can be provided. Flowable material can be inserted into the implant forming cavity. At least one of the first and second molds can be advanced toward the other of the first and second molds causing the flowable material to be urged against the first mold. Subsequent to curing of the flowable material, the temporary implant can be removed from the first mold. The temporary implant can include an integrally formed implant body and implant stem formed by the respective implant body forming cavity and the implant stem forming cavity.

The implant forming cavity can comprise a tibial component forming cavity. The implant forming cavity according to other features can include a femoral component forming cavity. According to additional features, the method can include threadably coupling a flowable material delivery device to a connection port provided on a first plate. Advancing can comprise progressively engaging teeth extending from rods with a second plate.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 2 is a perspective view of the cement mold assembly of FIG. 1 shown in an assembled position.

FIG. 3 is a cross-sectional view taken along lines 3-3 of FIG. 2.

FIG. 4 is a cross-sectional view taken along lines 4-4 of FIG. 2.

FIG. 5 is a cross-sectional view of the cement mold assembly shown subsequent to delivery of cement within the tibial component forming cavity.

FIG. 6 is an exploded bottom perspective view of a cement mold assembly constructed in accordance to additional features of the present disclosure.

FIG. 7 is a top perspective view of the cement mold assembly of FIG. 6 and further illustrating an optional reinforcement member configured to be molded as part of the resulting temporary implant.

Corresponding reference numerals indicate corresponding parts throughout the several views of the drawings.

DETAILED DESCRIPTION

Figure 1:
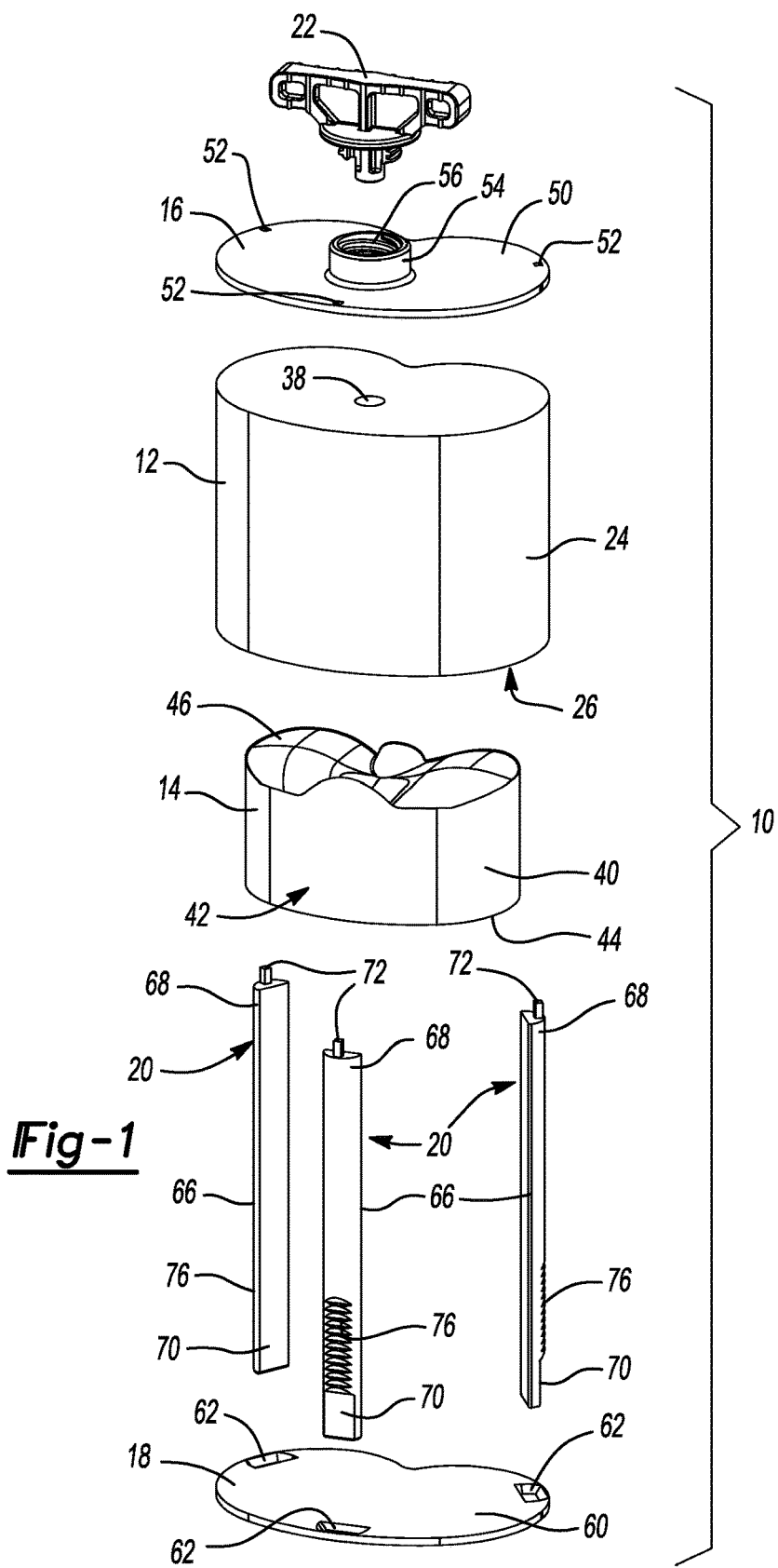
FIG. 1 is an exploded perspective view of a cement mold assembly constructed in accordance to one example of the present disclosure.
Figure 8:
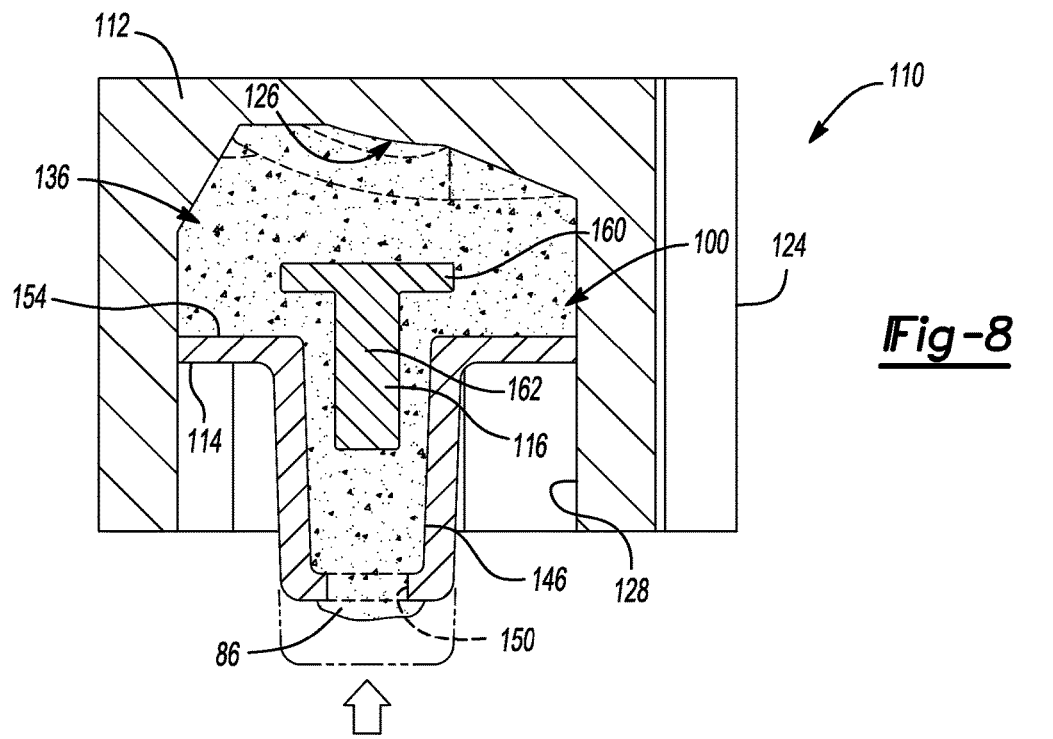
FIG. 8 is a cross-sectional view of the cement mold assembly of FIG. 6.
Figure 9:
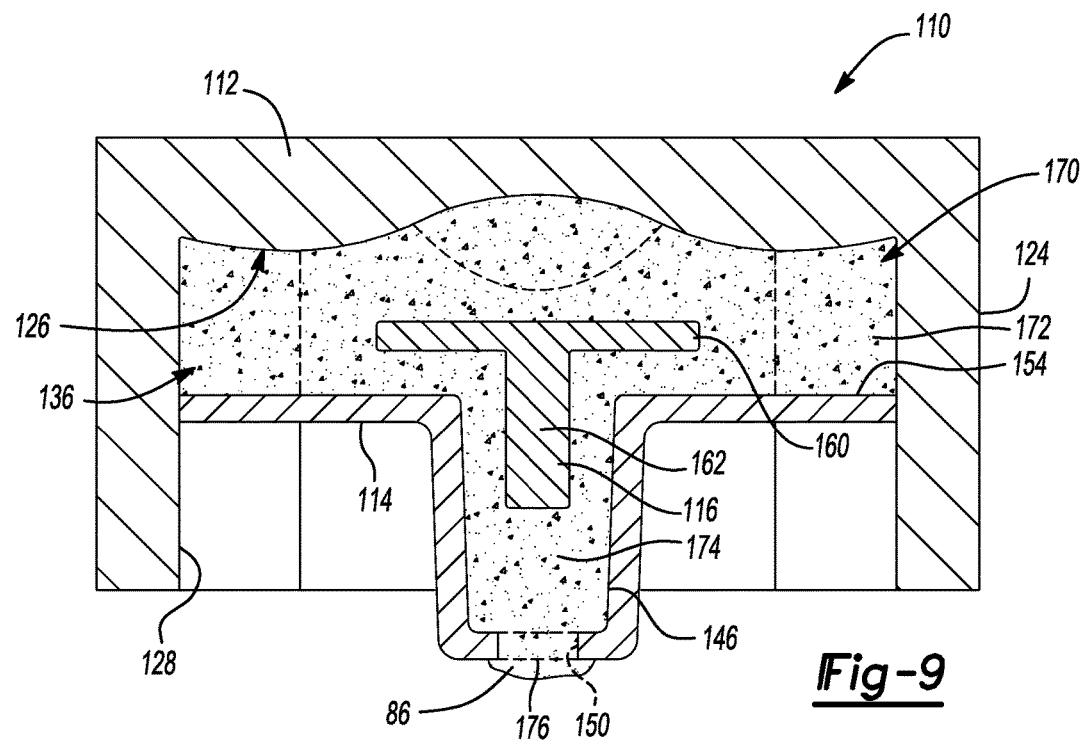
FIG. 9 is another cross-sectional view of the cement mold assembly of FIG. 6.

Example embodiments will now be described more fully with reference to the accompanying drawings.

The following description of the preferred embodiments concerning cement molds for temporary implants used during orthopedic surgical procedures are merely exemplary in nature and are not intended to limit the disclosure or its application or uses. Moreover, while the present invention is described in detail below with reference to cement molds for knee joints, it would be appreciated by those skilled in the art the present disclosure is clearly not limited to only cement molds for knee joints but may be utilized at various other areas for various other orthopedic surgical procedures. Therefore, it will be understood that the present description and the claims are applicable to any appropriate bone in the body. It will be understood that the terms "spacers" and "temporary implants" are used interchangeably throughout this disclosure to refer to the same component. A non-limiting discussion of terms and phrases intended to aid understanding of the present technology is provided at the end of this Detailed Description.

With initial reference to FIGS. 1-5, a cement mold assembly configured to form a temporary implant for use in delivering antibiotics to an infected site is shown and generally identified at reference numeral 10. The cement mold assembly 10 can generally include a first mold 12, a second mold 14, a first plate 16, a second plate 18, and a plurality of rods 20. The cement mold assembly 10 can further include a plug 22. As will become appreciated from the following discussion, the second mold 14 can be selectively and progressively advanced into the first mold 12 to create a unitary tibial component having a tibial tray portion and a stem portion.

The first mold 12 can generally include a first mold body 24 having an open end 26 and an inner wall 28. The first mold 12 can define a tibial component forming cavity 30 including a platform forming cavity 32 and a stem forming cavity 34. A first mold port 38 can be formed through the mold body 24 and aligned with the stem forming cavity 34.

The second mold 14 can include a second mold body portion 40 having an outer wall 42, an end surface 44 and a tibial platform forming surface 46. In one example, the tibial platform forming surface 46 can include contours configured to substantially replicate a corresponding tibial bearing surface. The dimensions of the outer wall 42 of the second mold body portion 40 are slightly less than the inner wall 28 of the first mold 12 such that the second mold 14 can be selectively and progressively advanced into the tibial component forming cavity 30.

The first plate 16 can include a first plate body portion 50 having a plurality of apertures 52. A first plate boss 54 can extend from the first plate 16. The first plate boss 54 can include a threaded delivery port 56. The second plate 18 can include a second plate body portion 60 having a plurality of apertures 62. Each of the rods 20 can generally be formed by an elongated body portion 66 having first ends 68 and second ends 70. A projection 72 can be formed at a distal tip of each of the first ends 68.

Teeth 76 can be formed along each of the elongated body portion 66. The second ends 70 can be received into the respective apertures 62 on the second plate 18. The projections 72 on the first ends 68 of the rods 20 can be received by the apertures 52 in the first plate 16. As will become appreciated herein, the teeth 76 can progressively engage the second plate body portion 60 at the respective apertures 62 upon progressive advancement of the second plate 18 toward the first plate 16 (resulting in the second mold 14 being progressively received within the first mold 12). In one example, the first and second molds 12 and 14 can be formed of silicone.

With particular reference now to FIGS. 4 and 5, a method of making a temporary implant for use in delivering antibiotics to an infected site using the mold assembly 10 will be described in greater detail. In one example, a surgeon can couple a flowable material delivery device 80 to the threaded delivery port 56 on the first plate 16. In one example, the flowable material delivery device 80 can include a handle (not specifically shown) that can be actuated to influence emission of flowable material 86 out of the delivery device 80 and into the tibial component forming cavity 30. Other configurations of the flowable material delivery device may be used. Furthermore, it will be appreciated that other connections may be made between the flowable material delivery device 80 and the respective port 38. For example, a luer lock coupling, a nozzle coupling or other coupling may be employed.

Once a sufficient amount of flowable material 86 has been advanced into the tibial component forming cavity 30, the flowable material delivery device 80 may be removed. Next, a surgeon can advance the second plate 18 toward the first plate 16 causing the second mold 14 to be progressively advanced into the tibial component forming cavity 30 of the first mold 12. It will be appreciated that continued advancement of the second mold 14 within the tibial component forming cavity 30 will control the resulting height or thickness of the resulting tibial platform formed by the tibial platform forming cavity 32. The thickness can be monitored such as by gradations 90 provided on the outer wall 42 of the second mold 14. The gradations 90 may be provided on other components of the cement mold assembly 10. Additionally or alternatively, a surgeon can deduce the thickness of the resulting tibial tray platform by the amount of teeth 76 that have been advanced through the respective aperture 62 on the second plate. It will further be appreciated that during such advancement, excess flowable material 86 will be expelled through the port 38 and out of the tibial component forming cavity 30.

Once the flowable material 86 has cured a sufficient amount, the mold assembly 10 can be removed from a resulting temporary implant 92. The resulting temporary implant 92 can include a tibial tray portion 94 and a stem portion 96. A portion 98 of cured flowable material 86 shown above the stem portion 96 may be discarded. The mold assembly 10 can be removed by any process such as by cutting away the first mold 12. Additionally or alternatively, a surgeon can retract the second mold 14 out of the tibial component forming cavity 30. Other methods are contemplated.

With reference now to FIGS. 6-9, a cement mold assembly configured to form a temporary implant for use in delivering antibiotics to an infected site constructed in accordance to additional features of the disclosure is shown and generally identified at reference numeral 110. The cement mold assembly 110 can generally include a first mold 112 and a second mold 114. According to one example, the mold assembly 110 can further incorporate an optional reinforcing member 116 (shown in FIGS. 7-9). As will become appreciated from the following discussion, the reinforcing member 116 can be used with the mold assembly 110 in instances where a solid reinforcing structure is to be molded within the temporary implant. As will be disclosed herein, the second mold 114 can be selectively and progressively advanced into the first mold 112 to create a unitary tibial component having a tibial tray portion and a stem portion.

The first mold 112 can generally include a mold body 124 having a first closed end 126 and a second open end 128. The mold body 124 can include a sidewall 130. The sidewall 130 can include gradations 132 formed thereon. The first mold 112 can define a cavity 136. The first mold 112 can be formed of transparent or semi-transparent material to observe formation of the temporary implant. Any of the other molds disclosed herein may also be formed of transparent or semi-transparent material.

The second mold 114 can include a second mold body 140 having an outer wall 142. The second mold 114 can further include a base portion 144 and a cannulated member 146 extending therefrom. The base portion 144 can have a footprint formed by the wall 142 that is complementary to the geometry of the sidewall 130 of the first mold 112. As will become appreciated from the following discussion, the second mold 114 can be slidably and progressively received by the sidewall 130 into the cavity 136 in a direction toward the first closed end 126. The cannulated member 146 can further define an inlet port 150 defined therethrough. In the example provided, the cannulated member 146 can have a generally rectangular cross-section. The base portion 144 of the second mold 114 can include a textured end surface 154. In one example, the textured end surface 154 can facilitate removal of the resulting tibial tray from the mold assembly 110 subsequent to formation. The first mold 112 can be formed of silicone. The second mold 114 can be formed of polyethylene.

The reinforcement member 116 can include a first lateral portion 160 that can generally oppose the first closed end 126 and a second longitudinal portion 162 that is generally received by the cannulated member 146. The reinforcement member 116 can be configured to be placed at least partially within the cavity 136 prior to progressive advancement of the second mold 114 into the cavity 136. The reinforcement member 116 can be configured to be molded into the resulting unitary tibial component. It will be appreciated that the geometry of the reinforcement member 116 is merely exemplary. In this regard, the reinforcement member 116 may be shaped in any configuration. Moreover, any of the temporary implants disclosed herein may be molded with a reinforcement member therein. The reinforcement member 116 can be formed of biocompatible metal.

An exemplary method of using the mold assembly 110 according to one example will now be described. While not specifically shown, a flowable material delivery device such as described above may be coupled at the port 150 to inject flowable material into the cavity 136 between the first and second molds 112 and 114. The second mold 114 can be advanced toward the first closed end 126 of the first mold 112 until the desired tibial tray thickness has been attained. It will be appreciated that additionally or alternatively the first mold 112 may be advanced toward the second mold 114. In some examples, a surgeon can reference the gradations 132 on the sidewall 130 of the first mold 112. The gradations 132 can be formed on the outer surface or inner surface of the sidewall 130. It will be appreciated that in some examples, excess flowable material may be expelled through the port 150.

Once the flowable material has cured a sufficient amount, the mold assembly 110 can be removed from a resulting temporary implant 170. The resulting temporary implant 170 can include a tibial tray portion 172 and a stem portion 174. A portion 176 of cured flowable material may be discarded. As identified above, the mold assembly 110 can be removed by any process.

Figure 10:
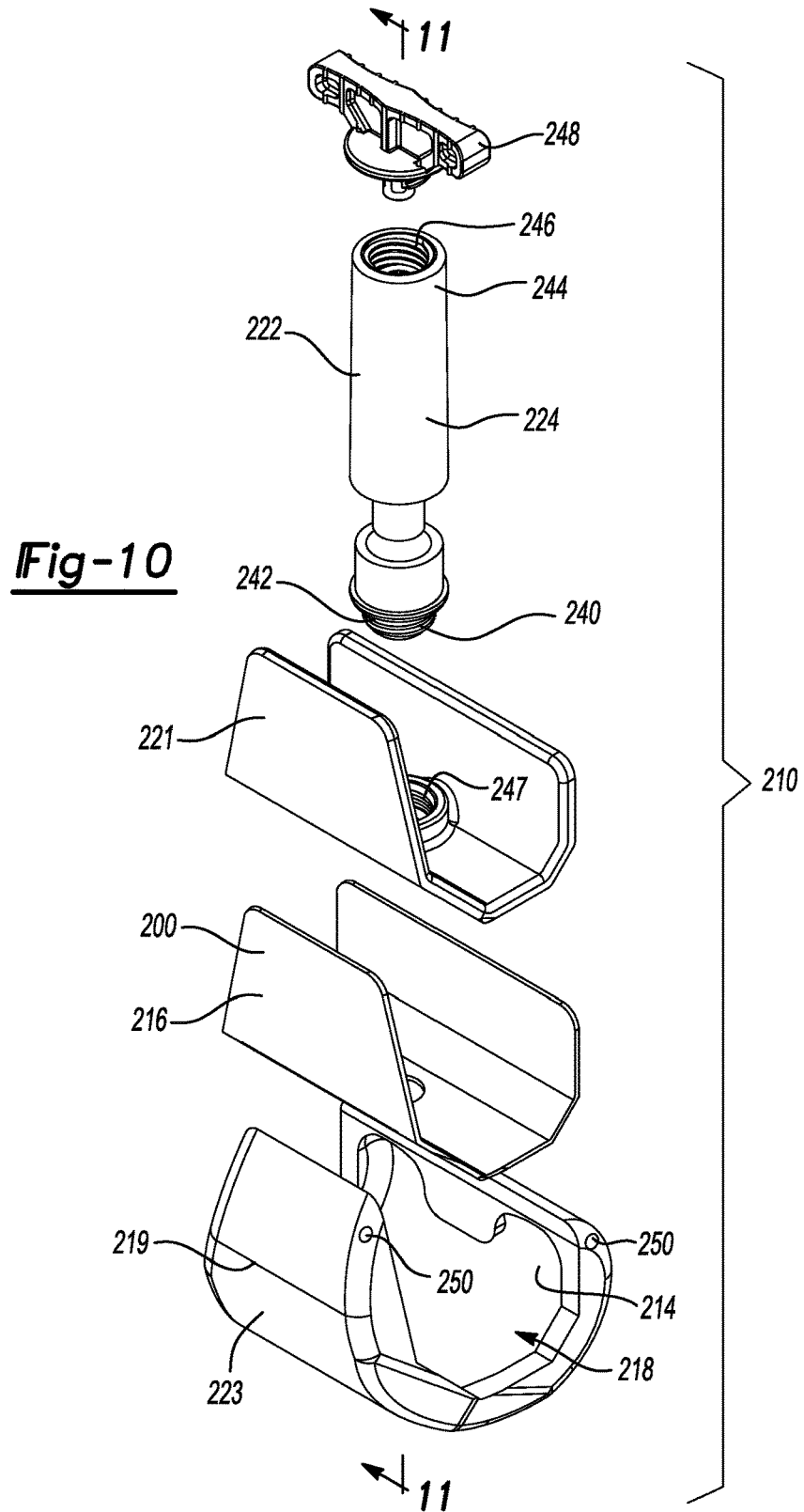
FIG. 10 is an exploded perspective view of a cement mold assembly constructed in accordance to further features of the present disclosure.
Figure 12:
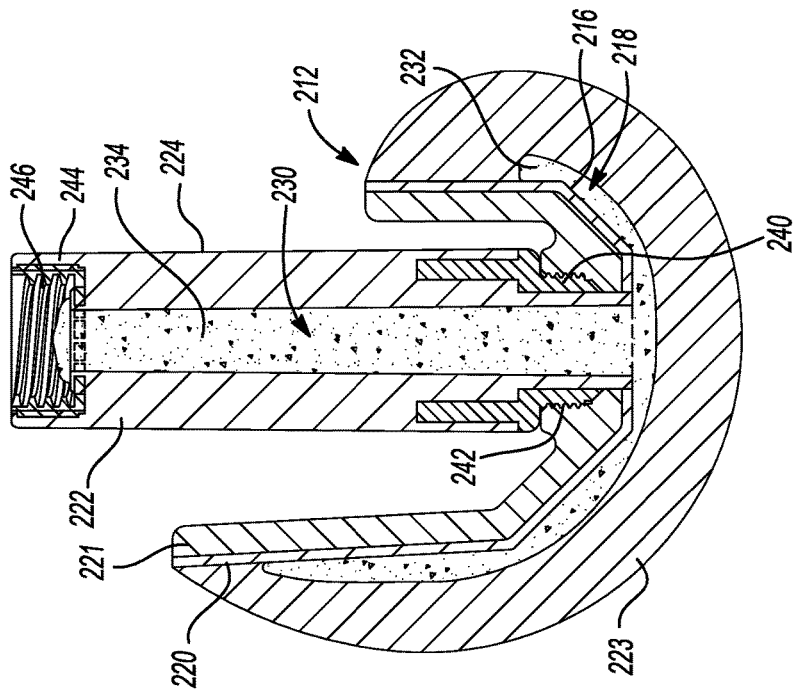
FIG. 12 is a cross-sectional view of the cement mold assembly of FIG. 11 shown subsequent to removing of a plug and introduction of flowable cement.
Figure 11:
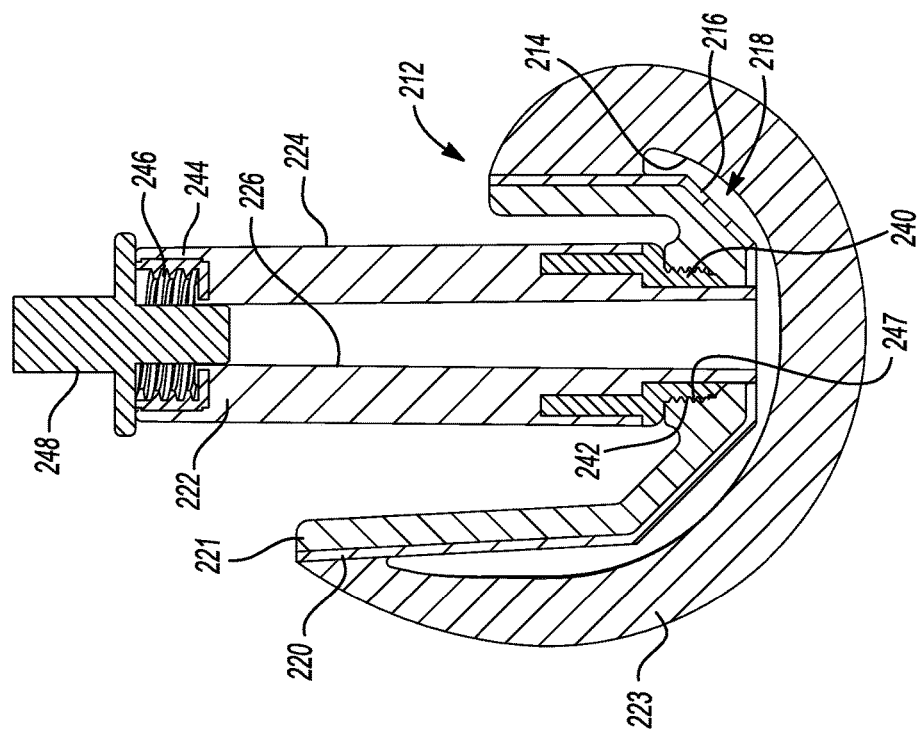
FIG. 11 is a cross-sectional view taken along lines 11-11 of FIG. 10.

With reference now to FIGS. 10-12, a cement mold assembly configured to form a temporary implant for use in delivering antibiotics to an infected site according to other features is shown and generally identified at reference numeral 210. The cement mold assembly 210 can include a mold body 212 (FIG. 11) having an outer sidewall 214 and an inner sidewall 216 that cooperate to define a cavity 218. The inner sidewall 216 can be operable to define a shape of the temporary implant.

The mold body 212 can be collectively formed by a first mold member 219, a second mold member 220, a third mold member 221 and a fourth mold member 222. The mold body 212 can include an articulating forming portion 223 and a stem forming portion 224. The cavity 218 is collectively defined by the articulating forming portion 223 and the stem forming portion 224. Specifically, the stem forming portion 224 includes an inner surface 226 that cooperates with the inner sidewall 216 in an assembled position (FIG. 11). The articulating forming portion 223 and the stem forming portion 224 can cooperate to form a unitary femoral component 230 (FIG. 12) having an articulating portion 232 formed by the articulating forming portion 223 and a stem portion 234 formed by the stem forming portion 224.

In one example, the stem forming portion 224 can be coupled to the articulating forming portion 223. In the example shown, the stem forming portion 224 is threadably coupled to the articulating forming portion 223. The stem forming portion 224 can have a first end 240 defining threads 242 and a second end 244 defining second threads 246. The first threads 242 can be configured to threadably couple with threads 247 on the third mold member 221. The second threads 246 can be configured to threadably couple with plug 248 or a cement delivery device (not shown). Flowable material may be injected into the cavity 218 similar to described above. In one example, the mold body 212 can define vents 250 configured to facilitate escaping air during delivery of the flowable material. It will be appreciated that vents may be additionally incorporated on any of the other molds disclosed herein. A reinforcement member, similar to the reinforcement member 116 (FIG. 7) can be optionally included as part of the cement mold assembly 210 for molding into the resulting unitary femoral component. The unitary femoral component 230 may be removed from the cement mold assembly 210.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Non-Limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

As used herein, the words "desire" or "desirable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on", "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

What is claimed is:

1. A cement mold assembly configured to form a temporary tibial knee implant for use in delivering antibiotics to an infected site, the cement mold assembly comprising:
    a first mold having a closed end and an inner wall extending from the closed end with the inner wall defining an open end of the first mold;
    a second mold receivable by the inner wall though the open end, and the second mold having a footprint complementary to and slidable along the inner wall;
    cooperatively engaging teeth operating to selectively and progressively index the first mold relative to the second mold while the second mold is being received by the first mold to permit any one of a plurality of tibial platform thicknesses to be selected;
    wherein the first mold cooperates with the second mold to form a cavity defining the temporary tibial knee implant including a stem portion formed by a stem forming cavity and a platform portion formed by a platform tray forming cavity having a selected thickness that corresponds to any one of the plurality of platform thicknesses that is selected.

2. The cement mold assembly of claim 1, wherein the first mold comprises a platform forming surface of the platform forming cavity, and the second mold comprises the stem forming cavity.

3. The cement mold assembly of claim 1, wherein the closed end of the first mold defines a cement fill port for the cavity.

4. The cement mold assembly of claim 1, further comprising a first plate and a second plate positioned outboard of the first and second molds, respectively.

5. The cement mold assembly of claim 4, further comprising at least two rods connected between the first and second plates, and wherein the at least two rods and the first and second plates include the cooperatively engaging teeth.

6. The cement mold assembly of claim 1, wherein selectively and progressively indexing of the second mold into the cavity urges excess cement out a fill port.

7. The cement mold assembly of claim 1, wherein the cavity comprises a textured surface adjacent the stem forming cavity.

8. The cement mold assembly of claim 1, wherein at least one of the first mold and the second mold comprises silicone.

9. The cement mold assembly of claim 1, further comprising a reinforcement member positioned at least partially within the cavity prior to progressively and selectively indexing the second mold into the cavity, wherein the reinforcement member is positioned to be molded into the temporary tibial knee implant.

10. The cement mold assembly of claim 9, wherein the reinforcement member comprises a first lateral portion received in the platform forming cavity and a second longitudinal portion received in the stem forming cavity.

11. The cement mold assembly of claim 1, wherein at least one of the first mold and the second mold includes gradations as an aid in identifying the selected thickness.

12. A cement mold assembly configured to form a temporary tibial knee implant for use in delivering antibiotics to an infected site, the cement mold assembly comprising:
    a first mold having a closed end and an inner wall extending from the closed end with the inner wall defining an open end of the first mold;
    a second mold receivable by the inner wall though the open end, and the second mold having a footprint complementary to and slidable along the inner wall; and
    cooperatively engaging teeth operating to selectively and progressively index the first mold relative to the second mold while the second mold is being received by the first mold to permit any one of a plurality of platform thicknesses to be selected; wherein the first mold cooperates with the second mold to form a cavity defining the temporary tibial knee implant including a stem portion formed by a stem forming cavity and a platform portion formed by a platform forming cavity having a selected thickness that corresponds to any one of the plurality of platform thicknesses that is selected, and wherein the first mold comprises a platform forming surface of the platform forming cavity, and the second mold comprises the stem forming cavity, and including a cement material delivery port on the exterior of the first mold.

13. The cement mold assembly of claim 12, wherein the closed end of the first mold defines a cement fill port for the cavity.

14. The cement mold assembly of claim 12, wherein selectively and progressively indexing of the second mold into the cavity urges excess cement out a fill port.

15. The cement mold assembly of claim 12, wherein the second mold comprises a textured surface adjacent the stem forming cavity.

16. The cement mold assembly of claim 12, wherein at least one of the first mold and the second mold comprises silicone.

17. The cement mold assembly of claim 12, wherein at least one of the first mold and the second mold includes gradations as an aid in identifying the selected thickness.

18. The cement mold assembly of claim 12, further comprising a reinforcement member positioned at least partially within the cavity prior to progressively and selectively indexing the second mold into the cavity, wherein the reinforcement member is positioned to be molded into the temporary tibial knee implant.

19. The cement mold assembly of claim 18, wherein the reinforcement member comprises a first lateral portion received in the platform forming cavity and a second longitudinal portion received in the stem forming cavity.

* * * * *